United States Patent
Marks

(10) Patent No.: US 8,530,518 B2
(45) Date of Patent: Sep. 10, 2013

(54) SALTS OF DIHYDROJASMONIC ACID AND USE THEREOF IN AGRICULTURE

(75) Inventor: David Marks, Liverpool (GB)

(73) Assignee: Plant Impact LLC, Preston (GB)

( * ) Notice: Subject to any disclaimer, the term of this patent is extended or adjusted under 35 U.S.C. 154(b) by 1461 days.

(21) Appl. No.: 11/587,371

(22) PCT Filed: Apr. 22, 2005

(86) PCT No.: PCT/GB2005/001562
§ 371 (c)(1),
(2), (4) Date: Jul. 23, 2007

(87) PCT Pub. No.: WO2005/102047
PCT Pub. Date: Nov. 3, 2005

(65) Prior Publication Data
US 2008/0032893 A1    Feb. 7, 2008

(30) Foreign Application Priority Data

Apr. 23, 2004 (GB) .................................. 0409011.4

(51) Int. Cl.
*A61K 31/557* (2006.01)

(52) U.S. Cl.
USPC ........................... 514/573; 562/477; 562/504

(58) Field of Classification Search
None
See application file for complete search history.

(56) References Cited

U.S. PATENT DOCUMENTS

| | | | |
|---|---|---|---|
| 4,060,535 A * | 11/1977 | Cinco | 554/75 |
| 5,728,866 A | 3/1998 | Rautenstrauch et al. | |
| 5,814,581 A | 9/1998 | Hirakawa et al. | |
| 6,114,284 A | 9/2000 | Fujisawa et al. | |
| 6,271,176 B1 | 8/2001 | Kamuro et al. | |
| 2005/0064001 A1 * | 3/2005 | Wiesman et al. | 424/405 |

FOREIGN PATENT DOCUMENTS

| | | |
|---|---|---|
| DE | 215 928 A1 | 11/1984 |
| DE | 221 059 A1 | 4/1985 |
| DE | 263 914 A1 | 1/1989 |
| DE | 276 025 A1 | 2/1990 |
| EP | 1 155 615 A1 | 11/2001 |
| JP | 03261743 | 11/1991 |
| RU | 2 163 776 C1 | 3/2001 |
| RU | 2 165 194 C1 | 4/2001 |
| RU | 2 198 545 C1 | 2/2003 |
| RU | 2 212 135 C2 | 9/2003 |
| RU | 2 212 137 C2 | 9/2003 |
| WO | 2 195 825 C1 | 1/2003 |
| WO | WO 03/020028 A2 | 3/2003 |

OTHER PUBLICATIONS

Reymond et al, Current Opinion in Plant Biology, Jasmonate and Salicylate as Global Signals for Defense Gene Expression, 1998, 1, pp. 404-411.*

Walden et al, Plant Physiology, Polyamines:Small Molecules Triggering Pathways in Plant Growth and Development, 1997, 113, pp. 1009-1013.*

* cited by examiner

*Primary Examiner* — Paul A Zucker

(74) *Attorney, Agent, or Firm* — Kilpatrick Townsend & Stockton LLP

(57) ABSTRACT

A compound comprising a water soluble salt of formula (I) wherein $R^1$ is a $C_{1-10}$alkyl group; or a $C_{2-10}$alkenyl group; M is a cation of valency n, provided that when $R^1$ is a pent-2-enyl group, $M^{n+}$ is other than sodium or potassium. These salts are particularly suitable for use in agricultural formulations. The formulations may further comprise benzoic acid derivatives and/or antioxidants.

22 Claims, 1 Drawing Sheet

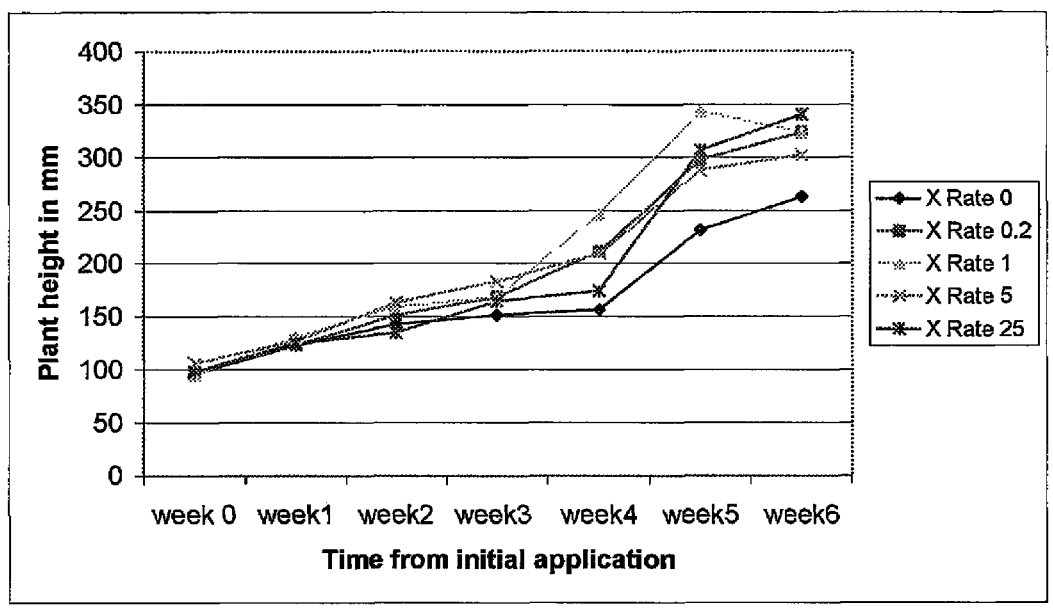

SALTS OF DIHYDROJASMONIC ACID AND USE THEREOF IN AGRICULTURE

The present invention relates to novel chemical compounds, to method of preparing these and to their use, in particular in agriculturally useful formulations.

When a plant encounters abiotic stress (this can be intense light, herbicide, ozone, heat, chilling, freezing, drought, salinity, flooding, and heavy metal toxicity), the plant increases production of reactive oxygen species (ROS) creating oxidative stress. ROS cause chemical damage to the cellular constituents of the plant.

If ROS build up to higher levels than the plant can cope with, protein lysis occurs within cells, and toxic ammonia can build up. This also happens when plants take up too much ammonium from the external environment (usually through fertilisation by urea or ammonium containing fertilisers) and is a major limiting factor in fertiliser use.

Jasmonic acid and similar compounds such as jasmonic acid, methyl jasmonate and dihydromethyl jasmonate, are known to stimulate a process called Induced systemic Resistance (ISR), which assists in producing stress and disease tolerance.

However, jasmonic acid and its derivatives are generally oils, which are immiscible in water, leading to formulation and application problems.

According to the present invention there is provided a water soluble salt of formula (I)

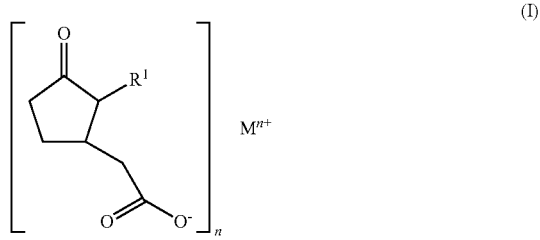

(I)

wherein $R^1$ is a $C_{1-10}$alkyl group, or a $C_{2-10}$alkenyl group; M is a cation of valency n, provided that when $R^1$ is a pent-2-enyl group, $M^{n+}$ is other than sodium or potassium.

In particular M is a metal cation, such as an alkali metal in particular potassium or sodium (where n is 1) or an alkaline earth metal such as magnesium where n is 2, provided that the salt formed therefrom is water soluble. Therefore M is suitably other than calcium. The salt may be in the form of a water miscible oil (such as the potassium and sodium salts) or it may be in the form of a sold, such as the magnesium salt.

M is preferably selected from potassium or magnesium, most preferably magnesium.

Alkyl or alkenyl groups $R^1$ may be straight or branched. Preferably however, $R^1$ is a straight chain alkyl or alkenyl group.

In a particular embodiment $R^1$ contains 5 carbon atoms. It is preferably selected from a pentyl group, making the compound of formula (I) a dihydrojasmonate salt, or a it is a pent-2-enyl group, so that the compound of formula (I) is a jasmonate salt.

Suitably, the compound of formula (I) is a water soluble salt of a derivative of dihydrojasmonic acid. A particularly preferred salt therefore is magnesium dihydrojasmonate. This salt has very good handling and flow properties, making it particularly useful in the context of agrochemical formulations.

BRIEF DESCRIPTION OF THE FIGURE

FIG. 1 is a graph showing the effect of a formulation of the invention on plant growth by root uptake.

Further according to the present invention there is provided a method for preparing a compound of formula (I), which method comprises reacting a compound of formula (II)

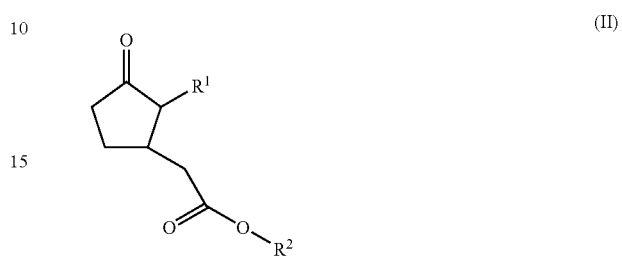

(II)

where $R^1$ is as defined in relation to formula (I) and $R^2$ is selected from hydrogen or a hydrocarbyl group, with a compound of formula (III)

$$M^{n+}(OR^3)_n \qquad (III)$$

where M and n are as defined in relation to formula (I), and $R^3$ is hydrogen or a $C_{1-3}$alkyl group such as methyl. The reaction is suitably effected in a solvent, which may be water, or an organic solvent such as an alkanol, in particular methanol or toluene.

Depending upon the particular salt being prepared, the reaction may be effected at moderate temperatures, for example from 0-50° C., conveniently at room temperature, or it may be conducted at elevated temperatures, for example from 50° C.-100° C., and conveniently at the reflux temperature of the solvent.

The product is suitably recovered either as a solid following evaporation of solvent, or it may be in the form of an aqueous solution, which is used directly in formulations.

As used herein, the term "hydrocarbyl" refers to organic moieties comprising carbon and hydrogen, such as alkyl, alkenyl, alkynyl, aryl or aralkyl groups such as benzyl. The term "alkyl" refers to straight or branched chains which suitably contain from 1 to 20, and preferably from 1 to 10 carbon atoms. Similarly the terms "alkenyl" and "alkynyl" refer to unsaturated hydrocarbyl groups, suitably containing from 2-20 and preferably from 2-10 carbon atoms. The term "aryl" refers to aromatic hydrocarbyl groups such as phenyl and naphthyl, whereas the term "aralkyl" refers to alkyl groups that are substituted with aryl groups such as benzyl.

In a particular embodiment, where $R^2$ is a hydrocarbyl group, it is selected from a $C_{1-10}$alkyl group, and suitably a $C_{1-6}$alkyl group such as methyl.

The compounds of formula (III) are known compounds such as potassium hydroxide, which may be used directly. Alternatively, the compound of formula (III) may be generated in situ. This may be particularly applicable where M is a magnesium salt, and where $R^3$ is a $C_{1-3}$alkyl group such as methyl. The applicants have found that a good way of preparing this compound is to react magnesium with an $C_{1-3}$alkanol such as methanol in the presence of a catalyst such as iodine. The reaction mixture is suitably heated to form the compound of formula (III) whereupon, a solution of the compound of formula (II) in the same alkanol is added and the reaction initiated.

The compounds of formula (II) are either known compounds or they may be prepared using conventional methods.

In the compounds of formula (II), $R^2$ is preferably hydrogen. Such compounds may be prepared by acidification of a compound of formula (II) where $R^2$ is a hydrocarbyl group.

Suitable reaction conditions will be apparent to a skilled chemist, but may include reacting the compound of formula (II) where $R^2$ is a hydrocarbyl group with a base such as sodium hydroxide, and then with an acid such as hydrochloric acid, as illustrated hereinafter.

Compounds of formula (I) may include a chiral center, and the invention includes all forms, including optically active forms, and mixtures thereof in all proportions including racemic mixtures.

Compounds of formula (I) are suitably used in agrochemical formulations in which the ISR properties may be desirable. The water-soluble nature of the compounds of the invention overcomes formulation problems and availability difficulties, which were present when conventional jasmonates have been employed in this way.

Thus in a further aspect, the invention provides a agriculturally acceptable composition comprising a compound of formula (I) and an agriculturally acceptable carrier.

The composition take various forms as is known in the art. For example, they include prills, dustable powders, soluble powders or tablets, water soluble granules, water dispersible granules, wettable powders, granules (slow or fast release), soluble concentrates, ultra low volume liquids, emulsifiable concentrates, dispersible concentrates, emulsions (both oil in water and water in oil), micro-emulsions, suspension concentrates, aerosols, capsule suspensions and seed treatment formulations. The composition type chosen in any instance will depend upon the particular purpose envisaged.

Agriculturally acceptable carriers used in the formulations may be solid of liquid depending upon the nature of the formulation.

For instance, solid diluents may include natural clays, kaolin, pyrophyllite, bentonite, alumina, montmorillonite, kieselguhr, chalk, diatomaceous earths, calcium phosphates, pumice, attapulgite clays, fuller's earth, ground corn cobs, sands, silicates, sodium, calcium or magnesium carbonates, sodium bicarbonate, magnesium sulphate, lime, flours, talc, polysaccharides and other organic and inorganic solid carriers.

Liquid diluents may include water or organic solvents such as a ketone, alcohol or glycol ether. These solutions may contain a surface-active agent (for example to improve water dilution or prevent crystallisation in a spray tank).

Compositions may additionally or alternatively include other types of reagent which are well known in the art, in particular, wetting agents, suspending agents and/or dispersing agents The compound of the present invention may be combined with other agrochemical compounds, either in the formulation or mixtures with other agrochemical compounds, such as herbicides, fungicides or plant growth regulators.

In particular however, the compounds of the invention, as well as closely related compounds, are combined with other reagents that reduce stress in plants and thereby enhance the effect of the compound of formula (I).

Thus, in a further aspect of the invention there is provided an agriculturally acceptable composition comprising (i) a compound comprising a water soluble salt of formula (IA)

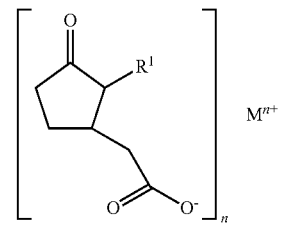

wherein $R^1$ is a $C_{1-10}$alkyl group, or a $C_{2-10}$alkenyl group; M is a cation of valency n, and (ii) a reagent that reduces stress in plants.

Particular examples of compounds of formula (IA) are compounds of formula (I) as defined above.

Reagents that reduce stress in plants include agriculturally acceptable compounds containing a benzoic acid group or derivatives thereof, of formula (V)

(V)

where $R^4$ is a group $OR^7$, $SR^7$ or $NR^7R^8$ where $R^7$ and $R^8$ are independently selected from hydrogen or hydrocarbyl, and $R^5$ and $R^6$ are independently selected from hydrogen, a hydrocarbyl group or a functional group, or $R^5$ and $R^5$ together with the carbon atoms to which they are attached form a fused ring system which may include one or more heteroatoms, selected from oxygen, nitrogen or sulphur.

In particular $R^4$ is a group $OR^9$ where $R^9$ is hydrogen or $C_{1-6}$alkyl such as methyl. Preferably $R^4$ is OH.

As used herein, the term "functional group" refers to reactive groups, in particular to electron withdrawing groups such as $OR^{10}$ or $C(O)R^{10}$ where $R^{10}$ hydrogen or $C_{1-6}$alkyl such as methyl.

Suitably $R^5$ and $R^6$ are hydrogen, or one is hydrogen and the other is a functional group, arranged at the ortho position on the ring, such as OH or $C(O)CH_3$.

Alternatively, $R^5$ and $R^6$ together with the carbon atoms to which they are attached, which are preferably adjacent carbon atoms, form a fused ring system, which is preferably ring containing 5 or 6 atoms, preferably 5 atoms, at least some of which are heteroatoms. The ring is suitably aromatic in nature. A particular example of a ring system of this type is 1,2,3-benzothiadiazole.

Particular examples of compounds of formula (V) include salicylic acid, acetyl salicylic acid (or 2-acetoxy benzoic acid), methyl salicylate, benzoic acid, and acibenzolar-S-methyl, as well as agriculturally acceptable salts thereof. Particular agriculturally acceptable salts include alkali metal salts such as potassium or sodium, alkaline earth metal salts such as calcium or magnesium, and some organic acid salts such as acetates.

These compounds have been shown to increase stress and disease resistance in plants by increasing the plant 'Systemic Acquired Resistance' (SAR) by stimulating production of phytoalexins and reducing ethylene (a stress hormone) synthesis.

However, these compounds they have the unwanted effect of increasing ROS, which cause damage to cells and create oxidative stress. This limits the effect of the compound because it makes it toxic if it builds up in the plant and ultimately becomes a limiting factor in its efficacy for giving abiotic stress tolerance. For instance, it is known that the efficacy of acetyl salicylic acid for giving stress tolerance is limited as it creates oxidative stress when used, and limits calcium flux into cytoplasm (which makes the cell less able to tolerate ammonia build up due to either protein lysis—increased by oxidative stress—or fertiliser use).

Similarly, although compounds of formula (I) such as jasmonate compounds can trigger ISR, their use can have the downside (if not moderated) of increasing ethylene production which under certain conditions weakens cell walls by increasing flux of calcium from cell walls into cytosol. Increasing cytoplasmic calcium helps the plant neutralise ammonia which builds up during prolonged abiotic stress, but if calcium is not available to replenish the cell wall calcium (held on calmodulin binding sites) the cell wall loses integrity and the plant is more susceptible to biotic stress.

Thus in a particularly preferred embodiment, the invention provides a composition which further comprises an antioxidant compound.

Particularly suitably antioxidants include arginine, or a polyamine for which arginine is a precursor such as putriscine, spermine, and spermidine. These compounds have antioxidant properties which can be used to combat ROS build-up during abiotic stress and are also involved in abiotic stress tolerance. A particularly preferred antioxidant is arginine.

In a particularly preferred embodiment, the invention provides a composition comprising (i) a compound of formula (I) above, (ii) a compound of formula (V) above and (iii) an antioxidant.

Preferred compounds of formula (I), (V) and antioxidants are as set out above. In particular, the compound of formula (I) is magnesium dihydrojasmonate, the compound of formula (V) is acetyl salicylic acid and the antioxidant is arginine.

In this composition, the compound of formula (I) may increase the formation of polyamines (spermine, spermidine, and putriscine), which are made from arganine (also supplied). The arginine gives immediate relief from oxidative stress, and ensures enough arganine is present to produce polyamines (which as well as being antioxidants, can perform a similar role to calcium in maintaining cell wall integrity, and so have a role in protecting the cell wall and controlling NH4 toxicity).

Furthermore, by supplying a combination of a compound of formula (I) with a compound of formula (V), the efficacy of the individual compounds may be improved, as ethylene build up is moderated.

The ratio of the components used in the composition will vary depending upon the precise nature of these components. For instance components (i) and (ii) will generally be present in a ratio of from 1:1 to 1:2 w/w.

The amount of antioxidant used may vary also, depending upon its nature. Antioxidants which have hormonal effects such as spermine, spermidine and putriscine may suitably be used quite sparingly, for example in an equivalent amount to component (i). Thus such compositions may have a composition comprising components (i):(ii):(iii) in a ratio of 1:1:1 to 1:2:1 w/w However, preferred antioxidants such as arginine, may be present in larger amounts for example up to 20 times as much as component (i). Thus a preferred composition in this case may have components (i): (ii):(iii) present in the range of from up to 1:2:20 or 1:1:20, for example from 1:1:10 to 1:2:10 w/w.

The components of the compositions may be combined together to form a concentrate that is then mixed with an agriculturally acceptable carrier such as water or a fertiliser before use. Such concentrates form a further aspect of the invention.

Compositions as described above can be used to enable a plant to maintain its growth and development during conditions of abiotic stress. By doing this the product will improve yield, quality, and reduce disease incidence during stress conditions. It does this by enhancing the plant's ability to cope with reactive oxygen species, and protein lysis which increases during abiotic stress conditions, and by maintaining cell wall integrity during abiotic stress conditions.

Thus in a further aspect, the invention provides a method for improving growth and/or yield and/or quality of higher plants during abiotic stress conditions, which method comprises applying to the plant or to the environment thereof, a compound of formula (I).

Preferably the compound of formula (I) is included in a composition as described above.

The compositions can be applied when stress conditions are occurring or when they are expected. Such conditions include intense light, herbicide, ozone, heat, chilling, freezing, drought, salinity, flooding, and heavy metal toxicity.

In particular, in some trials, compositions of the invention have been found reduce stress on plants growing in acidic soils, having a pH of less than 7, for example sandy acidic soils.

Furthermore, the compositions described above can provide an improvement in the performance of nitrogen fertilisers or fertilisers containing nitrogen where the nitrogen is derived from urea, amine (NH2) or ammonium (NH4). This includes both natural and synthetic fertilisers.

One of the major limiting factors in the rates of ammoniacal and ureic nitrogen that can be used is ammonia toxicity. By including a composition as described above into fertilisers at an appropriate rate, the plant's ability to tackle ammonia toxicity is improved, which means that the rate at which these fertilisers can be applied is increased.

Thus in a further aspect the invention provides a method for improving the performance of nitrogen fertilisers or fertilisers containing nitrogen, said method comprising applying said fertilisers to plants or to the environment thereof in combination with a compound of formula (I) as defined above. Again, the compound of formula (I) is suitably in a composition as described above, and in particular a composition comprising a compound of formula (V) and an antioxidant.

Fertiliser compositions including a composition as described above form a further aspect of the invention.

The compounds and compositions described above may also reducing of crop losses from biotic stress, caused for example by bacterial, viral and fungal pathogens.

Plants become more susceptible to disease when the cell wall deteriorates. Cell walls deteriorate during prolonged abiotic stress conditions, when calcium is moved from the cell wall to the cytoplasm. Compounds and compositions as described above will maintain a strong cell wall during abiotic stress conditions; this will decrease the likelihood of infection.

Thus in yet a further aspect, the invention provides a method for reducing crop losses from biotic stress, which method comprises administering to crops a compound of formula (I).

Preferably the compound of formula (I) is included in a composition as described above.

Compounds of formula (I) or compositions containing it as described above are suitably applied using conventional methods. For instance, the compositions are added to spray tanks, before spraying, or are added to drip irrigation reservoirs. In particular, compositions of the invention may suitably be applied to the roots of plants, for example as a root drench.

The amount of the compound or composition applied will vary depending upon factors such as the nature of the problem being treated, the crop and the conditions. However in general, the compound of formula (I) is applied to the crop in an amount of from between 0.005 to 0.5 g per hectare, for instance from 0.01 g and 0.1 g per hectare, per application.

Compounds and compositions described above can be used in the treatment of a wide range of crops, to reduce stress in the crops, and so provide growth benefits. Examples of crops include glass-house or protected crops, tree crops (such as pome and stone fruit crops, and nut crops such as walnuts, pistachio and olives, coco pods, palms such as oil palm and date palm, leafy crops such as tea as well of course as field crops such as cereals, for example wheat, tobacco, cotton, and vegetables such as brassicas for instance cabbages and lettuces, and root crops such as potatoes, carrots and sugar beet.

In particular the compounds and compositions described above can be used to treat crops that are subject to stress related disease. Particular examples of such crops include coco pods, which are subject to diseases such as black pod and cherrelle wilt.

The invention will now be particularly described by way of example with reference to the accompanying diagrammatic drawings in which FIG. 1 is a graph showing the results of the effects of a formulation of the invention on plant growth by root uptake in sandy acidic soil.

EXAMPLE 1

Preparation of Potassium Dihydrojasmonate Salt

Step 1

Formation of Dihydrojasmonic Acid from Methyldihydrojasmonate

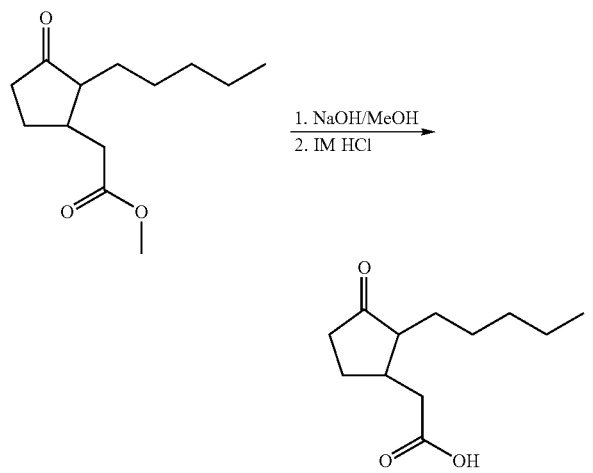

Sodium hydroxide pellets (82.6 g) were dissolved in methanol (425 ml) with stirring. This solution was added to a stirred solution of methyldihydrojasmonate (425 g)(obtained from F. D. Copeland) in methanol (425 ml). The reaction mixture was stirred at room temperature for 24 hours. After this time TLC analysis (10:90 ethylacetate EtOAc):Hexane) confirmed that all starting material had been consumed. Aqueous 1M hydrochloric acid solution was added slowly until the pH of the reaction mixture was ~1. The aqueous/methanol solution was extracted with ethyl acetate (4×150 ml) and the combined organic extracts were dried (MgSO$_4$) and evaporated under vacuum to give the dihydrojasmonic acid as a pale yellow oil (397.0 g, >99%).

The structure was confirmed using $^1$H and $^{13}$C NMR.

Step 2

Preparation of Dihydrojasmonic Acid Potassium Salt, 10% wt Aqueous Solution from Dihydrojasmonic Acid

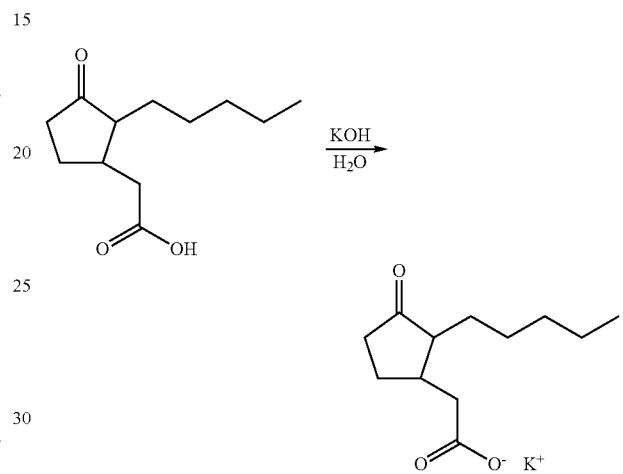

Potassium hydroxide (5.29 g) was dissolved in water (225 ml) with stirring. This was added to the dihydrojasmonic acid (20 g) prepared as described in step 1 to give a 10% wt aqueous solution of the dihydrojasmonic potassium salt.

The structure was confirmed using $^1$H and $^{13}$C NMR.

EXAMPLE 2

Alternative Preparation of Dihydrojasmonic Acid Potassium Salt

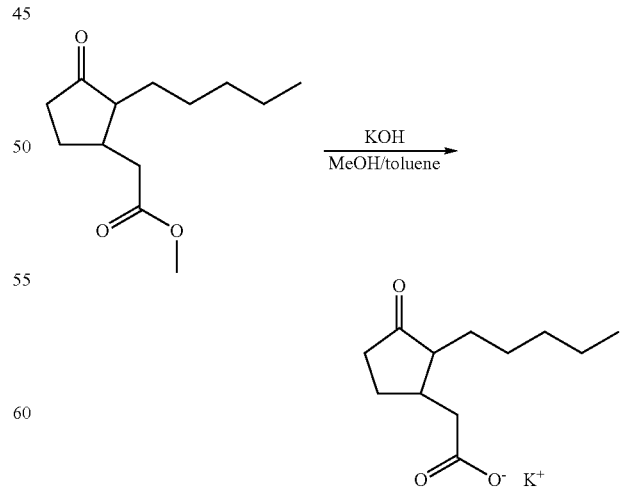

Methyldihydrojasmonate (10 g) was dissolved in toluene (100 ml) with stirring. 2M KOH solution in methanol (22.1 ml) was added and the solution brought to reflux. The reaction mixture was maintained at reflux for 18 hours after which time TLC analysis (10:90 EtOAc:hexane) indicated that no more starting material was present. The solvents were removed under vacuum to afford the dihydrojasmonic acid potassium salt as a yellow oil.

Toluene (3×100 ml) was added and removed under vacuum in an attempt to azeotrope off any residual water. However, the potassium salt remained as a yellow oil.

The structure was confirmed using $^1$H and $^{13}$C NMR.

EXAMPLE 3

Formation of Dihydrojasmonic Acid Sodium Salt from Methyldihydrojasmonate

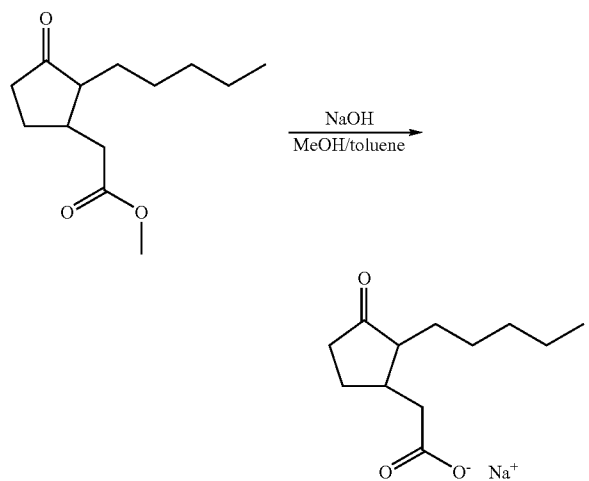

Sodium hydroxide pellets (3.53 g) were dissolved in methanol (20 ml) with stirring, before being added to a solution of the methyldihydrojasmonate (20 g) in toluene (20 ml). The reaction mixture was stirred at room temperature for 48 hours after which time TLC analysis (10:90 EtOAc:Hexane) indicated that no more starting material was present. The solvents were removed under vacuum to afford the dihydrojasmonic acid sodium salt as a yellow oil. Toluene (3×100 ml) was added and removed under vacuum in an attempt to azeotrope off any residue water. However, the sodium salt remained as a pale yellow oil.

EXAMPLE 4

Formation of Dihydrojasmonic Acid Magnesium Salt from Dihydrojasmonic Acid

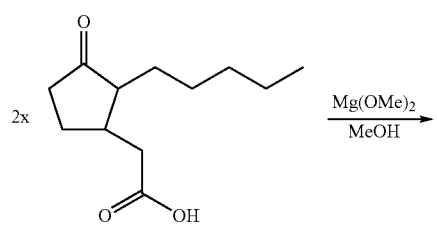

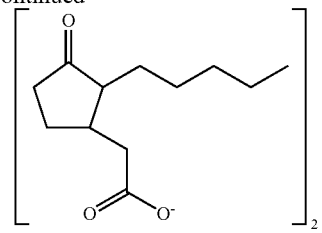

A two-necked 3 L round bottom flask was charged with magnesium turnings and methanol (700 ml) under nitrogen. Two crystals of iodine were added. Once the reaction had initiated stirring was commenced and the reaction mixture brought to reflux. The initially dark brown reaction mixture gradually became paler yellow in colour and a white precipitate began to form. Heating was continued until all the magnesium had reacted. At this point the reaction mixture consisted of a virtually colourless solution containing a white precipitate. The reaction mixture was cooled to room temperature before a solution of dihydrojasmonic acid (350 g) in methanol (700 ml) was added dropwise. The reaction mixture was then brought back to reflux, maintained at this temperature for two hours, and then stirred at room temperature overnight. This gave the reaction mixture as a clear pale yellow solution. The methanol was removed under vacuum to give the product as a pale yellow oil. Propan-2-ol (2×250 ml) was added and removed under vacuum to remove any residual water and this afforded the dihydrojasmonic acid magnesium salt (368 g, >99%) as a pale yellow solid.

The structure was confirmed using $^1$H and $^{13}$C NMR. The $^1$H NMR of the magnesium salt showed that the compound contained water. Karl Fisher analysis confirmed this and showed that the magnesium salt contained 1.8% water and residual propan-2-ol.

EXAMPLE 5

Agricultural Formulation

The following combination of components are suitably formulated together to form the following concentrates:

Formulation 1

| | |
|---|---|
| magnesium dihydrojasmonate | 100 g |
| acetyl salicylic acid | 100 g |
| arginine | 1000 g |

Formulation 2

| | |
|---|---|
| magnesium dihydrojasmonate | 100 g |
| sodium benzoate | 100 g |
| arginine | 100 g |

Formulation 3

| | |
|---|---|
| magnesium dihydrojasmonate | 100 g |
| sodium salicylate | 200 g |
| spermine | 100 g |

[SPELLING OF SALICYLATE CORRECTED HERE— OK?]

Formulation 4

| | |
|---|---|
| Magnesium dihydrojasmonate | 100 g |
| Sodium benzoate | 100 g |
| L-Arginine | 500 g |

These components are all water soluble powders and so the formulation can be carried out by straightforward mixing. The concentrate can then be mixed with a carrier such as water or a fertiliser and applied to plants such as crops, or to the environment thereof.

The combination of compounds in this formulation its designed to combat oxidative stress, whilst maintaining cell wall integrity. This gives increased tolerance to abiotic stress conditions, and has the added benefit of also expressing both SAR and ISR responses.

EXAMPLE 6

The effects of stress on plants treated with the formulation 4 was evaluated as a soil drench. The cultivar lettuce *Lactuca sativa* variety Arctic King was the species selected for test. Lettuce plants were grown individual pots in four different growth media, a low pH acidic sandy soil (pH 4.27), a high pH chalky clay soil (pH 9.35), Lufa 2.2 (pH 5.8) and rockwool growing blocks (inert).

Plants were stressed by high temperatures (30-35° C.) and low moisture levels which caused stunted and chlorotic growth especially in plants grown in sandy acidic soil. They were exposed to a light intensity of 3280 to 10320 Lux as required for good plant growth, with a light regime of 16 hours light/8 hours dark. Plants were only watered as required for them to retain turgidity.

Formulation 4 above was dissolved in water to produce formulation 5 as follows:

Formulation 5

| | |
|---|---|
| Distilled water | (99.93% w/w) |
| L-Arginine | (00.05% w/w) |
| Sodium benzoate | (00.01% w/w) |
| Magnesium dihydrojasmonate | (00.01% w/w) |

Formulation 5 was tested alone at the following rates—0 (control), 0.2x rate, 1x rate, 5x rate and 25x rate, the x rate being 500 ml product/ha. Assuming a plant density of 70,000 lettuce plants per hectare (literature) and an x rate of 500 mL product per Ha, each plant would then receive 7.14 mg/product. Dilutions of the product were made such that each plant received 7 mg (approx) in each daily dose for the x rate.

All treatments were applied to the test plants as aqueous solutions and to 10 replicates. Drench solutions applied to rockwool were made to volume with Hoaglands solution due to the lack of nutrients in this medium. Drench solutions for the three soils were made to volume in deionised water. 10 mL of solution applied to each plant saucer per day.

At each assessment interval (pre application and weekly thereafter) plants were assessed for height (mm), growth stage (BBCH) and phytotoxic effects. At the end of the study, root and shoot weights (fresh and dried) were taken.

The results are shown in Tables 1 to 5 and FIG. 1.

TABLE 1

Plant height (P/H) in mm (mean of 10 plants)

| | x Rate of Alethea | | | | | | | | | |
|---|---|---|---|---|---|---|---|---|---|---|
| | Control | | 0.2 | | 1 | | 5 | | 25 | |
| Soil type | P/H st[+] | P/H end | P/H st | P/H end | P/H st | P/H end | P/H st | P/H end | P/H st | P/H end |
| Sandy acidic | 96 | 263 | 98 | 324 | 95 | 324 | 106 | 303 | 98 | 341* |
| Chalky clay | 20 | 111 | 21 | 123 | 29 | 123 | 28 | 124 | 26 | 100 |
| Rockwool | 70 | 133 | 81 | 121 | 78 | 148 | 75 | 125 | 103 | 119 |
| Lufa 2.2 | 31 | 110 | 23 | 129 | 23 | 116 | 24 | 94 | 28 | 103 |

Note:
*significantly different from the control based on two-tailed test ($P \leq 0.05$)
[+]st represents start of test and "end" represents end of test

TABLE 2

Test plants growth stages (G/S) using BBCH code (mean of 10 plants)

| | x Rate of Alethea | | | | | | | | | |
|---|---|---|---|---|---|---|---|---|---|---|
| | Control | | 0.2 | | 1 | | 5 | | 25 | |
| Soil type | G/S st | G/S end | G/S st | G/S end | G/S st | G/S end | G/S st | G/S end | G/S st | G/S end |
| Sandy acidic | 16 | 56.5 | 16 | 56.5 | 16 | 56.5 | 16 | 47 | 16 | 57 |
| Chalky clay | 12.5 | 25.5 | 12.5 | 26 | 12.5 | 27 | 12.5 | 27 | 12.5 | 26 |

TABLE 2-continued

Test plants growth stages (G/S) using BBCH code (mean of 10 plants)

| | \multicolumn{10}{c}{x Rate of Alethea} |
| | Control | | 0.2 | | 1 | | 5 | | 25 | |
| Soil type | G/S st | G/S end | G/S st | G/S end | G/S st | G/S end | G/S st | G/S end | G/S st | G/S end |
|---|---|---|---|---|---|---|---|---|---|---|
| Rockwool | 17 | 34.8 | 17 | 37.6 | 17 | 41.8 | 17 | 37.1 | 17 | 32.3 |
| Lufa 2.2 | 13 | 26 | 13 | 26 | 13 | 26 | 13 | 26 | 13 | 26 |

TABLE 3

% chlorosis at final assessment timing

| | % chlorosis | | | |
|---|---|---|---|---|
| Treatment | Sandy acidic soil 41 days | Chalky clay 36 days | Lufa 2.2 43 days | Rock wool 43 days |
| Control | 58 | 52 | 21 | 49 |
| 0.2x | 56 | 50 | 15 | 39 |
| 1x | 55 | 38 | 18 | 49 |
| 5x | 55 | 33 | 20 | 51 |
| 25x | 54* | 36 | 19 | 49 |

Note:
*significantly different from the control based on two-tailed test (P ≦ 0.05)

TABLE 4

Mean dry shoot weights

| | Mean dry weights for shoots (g) | | | |
|---|---|---|---|---|
| Treatment | Sandy acidic soil | Chalky clay soil | Lufa 2.2 | Rockwool |
| Control | 5.74 | 2.89 | 3.16 | 6.13 |
| 0.2x | 7.01 | 3.77 | 3.06 | 6.48 |
| 1x | 6.68 | 3.13 | 3.05 | 3.67* |
| 5x | 5.89 | 3.19 | 2.21 | 6.13 |
| 25x | 6.14 | 4.15 | 2.77 | 5.18 |

Note:
*significantly different from the control based on two-tailed test (P ≦ 0.05)

TABLE 5

Mean dry root weights

| | Mean dry weights for roots (g) | | | |
|---|---|---|---|---|
| Treatment | Sandy acidic soil | Chalky clay soil | Lufa 2.2 | Rockwool |
| Control | 2.77 | 2.00 | 1.25 | N/A |
| 0.2x | 2.61 | 2.43 | 1.07 | N/A |
| 1x | 2.28 | 2.04 | 1.07 | N/A |
| 5x | 2.62 | 2.52 | 1.04 | N/A |
| 25x | 2.61 | 2.97 | 1.26 | N/A |

Toxcalc V 05 was used to determine any statistically significant difference between treated and control plants.

A significant improvement in plant health over untreated ones was observed with the 25x (12.5 L/ha) treatment to plants in sandy acidic soil 41 days after the first application. The improvements were to plant height (341 mm compared to 263 mm in the control) (see also FIG. 1) and a reduction in phytotoxicity (54% chlorosis compared to 58% in the control). Formulation applied at all rates as a drench to plants in sandy acidic soil improved plant height (by 23%, 23% 15% and 30% at 100 mL/ha, 500 mL/ha, 2500 mL/ha and 12500 mL/ha respectively) and increased mean dry shoot weight (by 22%, 16%, 3% and 7% at 100 mL/ha, 500 mL/ha, 2500 mL/ha and 12500 mL/ha respectively).

The growth medium that was seen to stress the plants most, the sandy acidic soil was selected for use in a foliar application test. Foliar applications were applied with the use of a hand sprayer to ensure an even coverage and were sprayed on the leaves until incipient run-off. However, treated plants showed no statistically significant improvement in health or alleviation of stress when compared to untreated plants at all rates tested.

In this trial therefore, formulation 5 produced an improvement in plant height and reduction of stress (chlorosis) was seen in plants grown in sandy acidic soil, when applied by root uptake.

The invention claimed is:

1. An agriculturally acceptable composition comprising:
  (i) a compound that is a water soluble or water-miscible salt of the formula

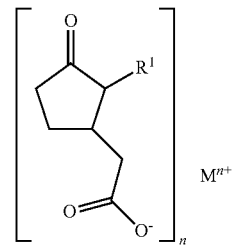

wherein $R^1$ is a member selected from the group consisting of pentyl and pent-2-enyl, M is a cation of valency n and a member selected from the group consisting of potassium in which case n is 1, sodium in which case n is 1, and magnesium in which case n is 2;
  (ii) a reagent that reduces stress in plants and is a member selected from the group consisting of salicylic acid, acetyl salicylic acid, metyl salicylate, benzoic acid, acibenzolar-S-methyl, and agriculturally acceptable salts thereof; and
  (iii) an antioxidant selected from the group consisting of arginine and a polyamine for which arginine is a precursor.

2. The composition of claim 1 wherein M is potassium or magnesium.

3. The composition of claim 1 wherein M is magnesium.

4. The composition of claim 1 wherein $R^1$ is n-pentyl.

5. The composition of claim 1 wherein said reagent is a member selected from the group consisting of acetyl salicylate, sodium salicylate, and sodium benzoate.

6. The composition of claim 1 wherein said compound is potassium dihydrojasmonate.

7. The composition of claim 1 wherein said compound, said reagent, and said antioxidant are at a weight ratio of from 1:1:1 to 1:2:20.

8. The composition of claim 1 further comprising an agriculturally acceptable carrier.

9. A method for improving one or more of growth, yield, and quality of higher plants during abiotic stress conditions, said metod comprising applying to said plants or to the environment of said plants a composition according to claim 1.

10. A method for improving the performance of nitrogen fertilizers or fertilizers containing nitrogen, said method comprising applying said fertilizers to plants or to the environment of said plants in combination with a composition according to claim 1.

11. A method for reducing crop losses from abiotic stress, said method comprising administering to said crops or to the environment of said crops a composition according to claim 1.

12. A fertilizer compostion comprising a composition according to claim 1.

13. A concentrate comprising:
(i) a compound that is a water-soluble or water-miscible salf of formula

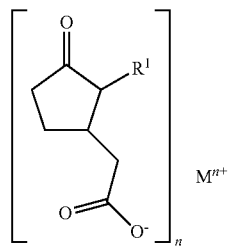

wherein $R^1$ is a member selected from the group consisting of pentyl and pent-2-enyl, M is a cation of valency n and a member selected from the group consisting of potassium in which case n is 1, sodium in which case n is 1, and magnesium in which case n is 2; and
(ii)
a reagent that reduces stress in plants and is a member selected from the group consisting of salicylic acid, acetyl salicylic acid, metyl salicylate, benzoic acid, acibenzolar-S-methyl, and agriculturally acceptable salts thereof; and
(iii) an antioxidant selected from the group consisting of arginine and a polyamine for which arginine is a precursor.

14. An agriculturally acceptable composition comprising:
(i) a compound that is a water-soluable or water-miscible salt of formula

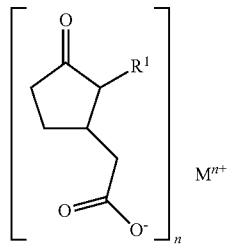

wherein $R^1$ is pent-2-enyl, M is a cation of magnesium, and n is 2,
(ii) a reagent that reduces stress in plants and is acetyl salicylic acid, and
(iii) an antioxidant that is arginine.

15. The compistion of claim 14 wherein said water-soluble or water-miscible salt, said acetyl salicylic acid, and said arginine are at a weight ratio of from 1:1:1 to 1:2:20.

16. A method for improving one or more of growth, yield, and quality of higher plants during abiotic stress conditions, said method comprising applying to said plants or to the environment of said plants a composition according to claim 14.

17. A method for improving the performance of nitrogen fertilizers or fertilizers containing nitrogen, said method comprising applying said fertilizers to plants or to the environment of said plants in combination with a composition according to claim 14.

18. A method for reducing crop losses from abiotic stress, said method comprising administering to said crops or to the environment of said crops a composition according to claim 14.

19. A fertilizer comprising a composition according to claim 14.

20. A concentrate comprising a composition according to claim 14.

21. An agriculturally acceptable composition comprising:
(i) potassium dihydrojasmonate,
(ii) sodium benzoate, and
(iii) arginine.

22. The composition of claim 21 wherein said potassium dihydrojasmonate, said sodium benzoate, and said arginine are at a weight ratio of from 1:1:1 to 1:2:20.

* * * * *